United States Patent
Nagao (10) Patent No.: US 11,540,700 B2
(45) Date of Patent: Jan. 3, 2023

(54) MEDICAL SUPPORTING ARM AND MEDICAL SYSTEM

(71) Applicant: SONY CORPORATION, Tokyo (JP)

(72) Inventor: Daisuke Nagao, Kanagawa (JP)

(73) Assignee: SONY CORPORATION, Tokyo (JP)

(*) Notice: Subject to any disclaimer, the term of this patent is extended or adjusted under 35 U.S.C. 154(b) by 403 days.

(21) Appl. No.: 16/341,315

(22) PCT Filed: Oct. 12, 2017

(86) PCT No.: PCT/JP2017/036976
§ 371 (c)(1),
(2) Date: Apr. 11, 2019

(87) PCT Pub. No.: WO2018/088105
PCT Pub. Date: May 17, 2018

(65) Prior Publication Data
US 2019/0274524 A1   Sep. 12, 2019

(30) Foreign Application Priority Data

Nov. 10, 2016  (JP) ............................. JP2016-219521

(51) Int. Cl.
*A61B 1/00* (2006.01)
*A61B 1/04* (2006.01)
(Continued)

(52) U.S. Cl.
CPC ............ *A61B 1/00149* (2013.01); *A61B 1/00* (2013.01); *A61B 1/00006* (2013.01);
(Continued)

(58) Field of Classification Search
CPC combination set(s) only.
See application file for complete search history.

(56) References Cited

U.S. PATENT DOCUMENTS

| 5,515,478 A | * | 5/1996 | Wang ..................... A61B 34/70 |
| | | | 700/262 |
| 5,876,325 A | * | 3/1999 | Mizuno ............. A61B 1/00188 |
| | | | 600/102 |

(Continued)

FOREIGN PATENT DOCUMENTS

| JP | 08-117238 A | 5/1996 |
| JP | 10-249769 A | 9/1998 |

(Continued)

OTHER PUBLICATIONS

International Search Report and Written Opinion of PCT Application No. PCT/JP2017/036976, dated Dec. 12, 2017, 06 pages of ISRWO.

*Primary Examiner* — Anh Tuan T Nguyen
*Assistant Examiner* — Shankar Raj Ghimire
(74) *Attorney, Agent, or Firm* — Chip Law Group (57) ABSTRACT

A medical supporting arm according to the present disclosure includes a supporting arm and a calculation unit. The supporting arm supports an oblique-viewing endoscope. The calculation unit calculates a rotation angle of the oblique-viewing endoscope around an axis in a longitudinal direction, and an insertion amount of the oblique-viewing endoscope into a human body on the basis of a first expression that defines coordinates of a subject in a coordinate system in which an insertion opening allowing the oblique-viewing endo scope to be inserted into the human body serves as an origin, and a second expression that defines the coordinates of the subject positioned in an optical axis direction of an objective lens disposed at a distal end of the oblique-viewing endoscope in a coordinate system in which the distal end of the oblique-viewing endoscope serves as an origin.

11 Claims, 7 Drawing Sheets

(51) Int. Cl.
*A61B 1/313* (2006.01)
*A61B 5/06* (2006.01)
*G02B 23/24* (2006.01)
*A61B 90/50* (2016.01)

(52) U.S. Cl.
CPC .......... *A61B 1/00179* (2013.01); *A61B 1/042* (2013.01); *A61B 1/3132* (2013.01); *A61B 5/065* (2013.01); *A61B 90/50* (2016.02); *G02B 23/24* (2013.01)

(56) References Cited

U.S. PATENT DOCUMENTS

| | | | | |
|---|---|---|---|---|
| 6,120,433 | A * | 9/2000 | Mizuno | A61B 34/70 600/102 |
| 6,858,003 | B2 * | 2/2005 | Evans | A61B 34/32 606/1 |
| 8,251,890 | B2 * | 8/2012 | Tanaka | A61B 5/06 600/103 |
| 8,298,135 | B2 * | 10/2012 | Ito | A61B 1/00009 600/117 |
| 2002/0133173 | A1 * | 9/2002 | Brock | A61B 34/70 606/130 |
| 2003/0220541 | A1 * | 11/2003 | Salisbury, Jr. | A61B 34/30 600/101 |
| 2006/0020279 | A1 * | 1/2006 | Chauhan | A61B 34/30 606/167 |
| 2007/0083098 | A1 * | 4/2007 | Stern | A61B 34/35 600/407 |
| 2011/0071347 | A1 * | 3/2011 | Rogers | A61B 34/30 600/104 |
| 2011/0071544 | A1 * | 3/2011 | Steger | A61B 1/313 606/130 |
| 2013/0250081 | A1 * | 9/2013 | Pandey | A61B 1/00183 348/77 |
| 2015/0313452 | A1 * | 11/2015 | Hasser | A61B 34/30 600/102 |
| 2015/0359419 | A1 * | 12/2015 | Hane | A61B 1/00011 600/117 |
| 2016/0195706 | A1 * | 7/2016 | Fujii | G02B 23/26 362/551 |
| 2016/0213364 | A1 * | 7/2016 | Inoue | A61B 1/0052 |
| 2017/0172662 | A1 * | 6/2017 | Panescu | A61B 34/20 |
| 2018/0263710 | A1 * | 9/2018 | Sakaguchi | A61B 34/70 |
| 2018/0280110 | A1 * | 10/2018 | Meglan | A61B 1/00048 |
| 2018/0296074 | A1 * | 10/2018 | Trulson | G02B 21/361 |
| 2019/0159661 | A1 * | 5/2019 | Itkowitz | A61B 1/00149 |

FOREIGN PATENT DOCUMENTS

| | | | |
|---|---|---|---|
| JP | 2003-310638 A | 11/2003 | |
| WO | WO-2010083480 A2 * | 7/2010 | ............. A61B 34/30 |
| WO | 2016/017532 A1 | 2/2016 | |
| WO | WO-2017070610 A1 * | 4/2017 | ......... G02B 23/2446 |

* cited by examiner

MEDICAL SUPPORTING ARM AND MEDICAL SYSTEM

CROSS REFERENCE TO RELATED APPLICATIONS

This application is a U.S. National Phase of International Patent Application No. PCT/JP2017/036976 filed on Oct. 12, 2017, which claims priority benefit of Japanese Patent Application No. JP 2016-219521 filed in the Japan Patent Office on Nov. 10, 2016. Each of the above-referenced applications is hereby incorporated herein by reference in its entirety.

TECHNICAL FIELD

The present disclosure relates to a medical supporting arm and a medical system.

BACKGROUND ART

Conventionally, for example, Patent Literature 1 below has described a medical observation device including an imaging unit that picks up an image of a surgical region, and a holding unit that is connected to the imaging unit and is provided with rotary shafts such that the rotary shafts are operable with at least six degrees of freedom. At least two of the rotary shafts are active shafts whose driving is controlled on the basis of the states of the rotary shafts, and at least one of them is a passive shaft that rotates according to a direct external operation accompanying contact.

CITATION LIST

Patent Literature

Patent Literature 1: WO 2016/017532

DISCLOSURE OF INVENTION

Technical Problem

Incidentally, even if an endoscope that is inserted into the human body has an obstacle in front of an observation target object, the use of an oblique-viewing endoscope enables the observation target object to be observed without being hidden by the obstacle. However, it is extremely difficult for a surgeon to position an observation target object at the center of a picked up image while operating an oblique-viewing endoscope.

Patent Literature 1 above describes point lock observation with a medical microscope, but the technology described in Patent Literature 1 takes nothing into consideration about supporting an oblique-viewing endoscope by using a specific part such as the abdominal wall as a constraint condition in the case where the oblique-viewing endoscope is inserted into the human body.

Accordingly, it is desired to always have an observation target object within the region of a picked up image in the case where an oblique-viewing endoscope is inserted into the human body for operation.

Solution to Problem

According to the present disclosure, there is provided a medical supporting arm including: a supporting arm configured to support an oblique-viewing endoscope; and a calculation unit configured to calculate a rotation angle of the oblique-viewing endoscope around an axis in a longitudinal direction, and an insertion amount of the oblique-viewing endoscope into a human body on the basis of a first expression that defines coordinates of a subject in a coordinate system in which an insertion opening allowing the oblique-viewing endoscope to be inserted into the human body serves as an origin, and a second expression that defines the coordinates of the subject positioned in an optical axis direction of an objective lens disposed at a distal end of the oblique-viewing endoscope in a coordinate system in which the distal end of the oblique-viewing endoscope serves as an origin.

In addition, according to the present disclosure, there is provided a medical system including: a camera head including an imaging unit that images a subject; an oblique-viewing endoscope configured to be inserted into a human body, and be capable of rotating around an axis in an insertion direction with respect to the camera head; a supporting arm configured to support the oblique-viewing endoscope; and an arm controlling apparatus configured to control the supporting arm. The arm controlling apparatus includes a calculation unit configured to calculate a rotation angle of the oblique-viewing endoscope around an axis in a longitudinal direction, and an insertion amount of the oblique-viewing endoscope into a human body on the basis of a first expression that defines coordinates of the subject in a coordinate system in which an insertion opening allowing the oblique-viewing endoscope to be inserted into the human body serves as an origin, and a second expression that defines the coordinates of the subject positioned in an optical axis direction of an objective lens disposed at a distal end of the oblique-viewing endoscope in a coordinate system in which the distal end of the oblique-viewing endoscope serves as an origin.

Advantageous Effects of Invention

According to the present disclosure as described above, it is possible to always have an observation target object within the region of a picked up image in the case where an oblique-viewing endoscope is inserted into the human body for operation.

Noted that the effects described above are not necessarily limitative. With or in the place of the above effects, there may be achieved any one of the effects described in this specification or other effects that may be grasped from this specification.

MODE(S) FOR CARRYING OUT THE INVENTION

Hereinafter, (a) preferred embodiment(s) of the present disclosure will be described in detail with reference to the appended drawings. It is to be noted that, in this specification and the appended drawings, structural elements that have substantially the same function and structure are denoted with the same reference numerals, and repeated explanation of these structural elements is omitted.

Figure 1:
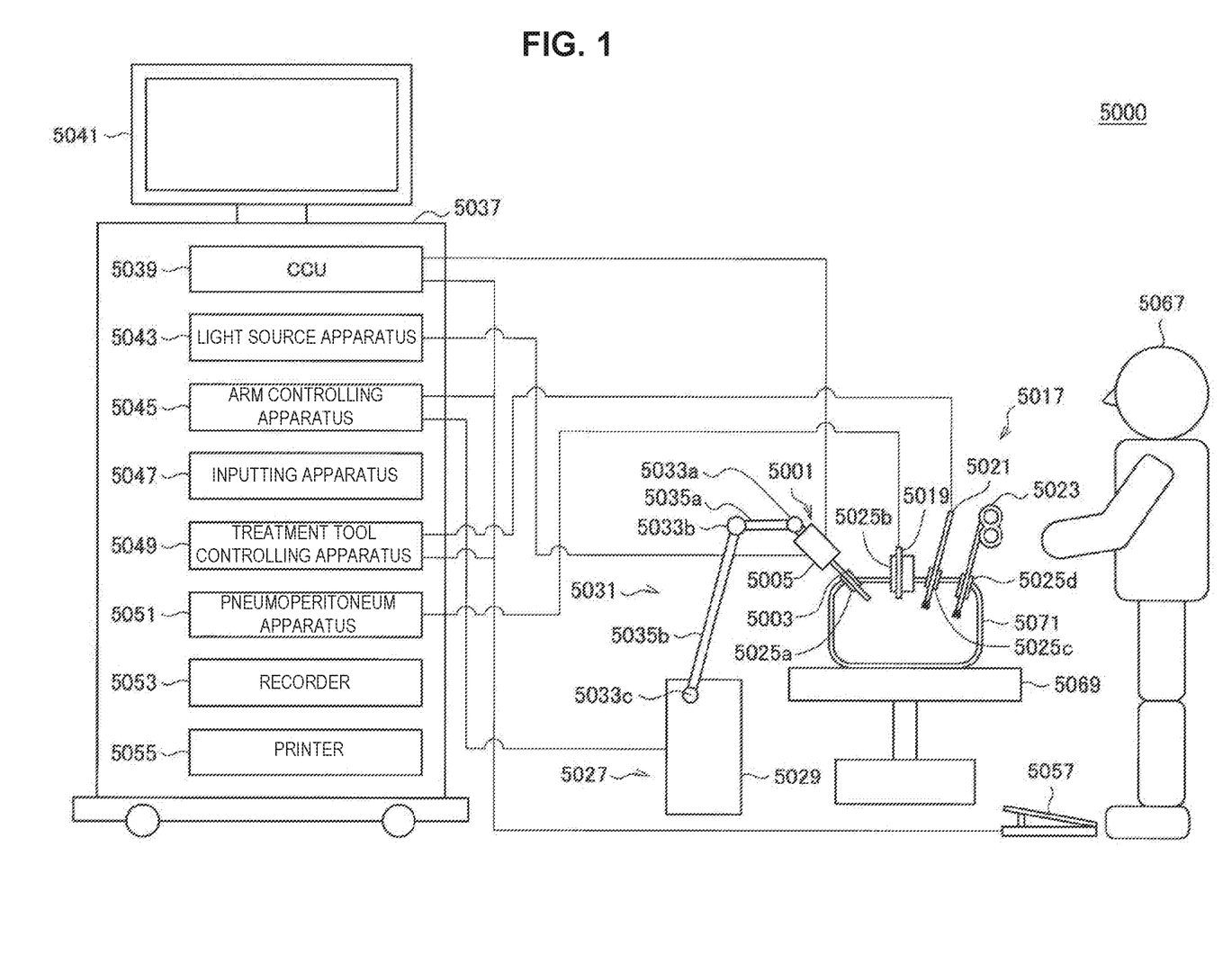
FIG. 1 is a view depicting an example of a schematic configuration of an endoscopic surgery system to which technology of according to the present disclosure can be applied.

Noted that the description will proceed in the following order.
1. Configuration Example of Endoscope System
2. Basic Configuration of Oblique-Viewing Endoscope
3. Control over Oblique-Viewing Endoscope according to the Present Embodiment
1. Configuration Example of Endoscope System FIG. 1 is a view depicting an example of a schematic configuration of an endoscopic surgery system 5000 to which the technology according to an embodiment of the present disclosure can be applied. In FIG. 1, a state is illustrated in which a surgeon (medical doctor) 5067 is using the endoscopic surgery system 5000 to perform surgery for a patient 5071 on a patient bed 5069. As depicted, the endoscopic surgery system 5000 includes an endoscope 5001, other surgical tools 5017, a supporting arm apparatus 5027 which supports the endoscope 5001 thereon, and a cart 5037 on which various apparatus for endoscopic surgery are mounted.

In endoscopic surgery, in place of incision of the abdominal wall to perform laparotomy, a plurality of tubular aperture devices called trocars 5025a to 5025d are used to puncture the abdominal wall. Then, a lens barrel 5003 of the endoscope 5001 and the other surgical tools 5017 are inserted into body cavity of the patient 5071 through the trocars 5025a to 5025d. In the example depicted, as the other surgical tools 5017, a pneumoperitoneum tube 5019, an energy device 5021 and forceps 5023 are inserted into body cavity of the patient 5071. Further, the energy device 5021 is a treatment tool for performing incision and peeling of a tissue, sealing of a blood vessel or the like by high frequency current or ultrasonic vibration. However, the surgical tools 5017 depicted are mere examples at all, and as the surgical tools 5017, various surgical tools which are generally used in endoscopic surgery such as, for example, tweezers or a retractor may be used.

An image of a surgical region in a body cavity of the patient 5071 imaged by the endoscope 5001 is displayed on a display apparatus 5041. The surgeon 5067 would use the energy device 5021 or the forceps 5023 while watching the image of the surgical region displayed on the display apparatus 5041 on the real time basis to perform such treatment as, for example, resection of an affected area. It is to be noted that, though not depicted, the pneumoperitoneum tube 5019, the energy device 5021 and the forceps 5023 are supported by the surgeon 5067, an assistant or the like during surgery.
(Supporting Arm Apparatus)

The supporting arm apparatus 5027 includes an arm unit 5031 extending from a base unit 5029. In the example depicted, the arm unit 5031 includes joint portions 5033a, 5033b and 5033c and links 5035a and 5035b and is driven under the control of an arm controlling apparatus 5045. The endoscope 5001 is supported by the arm unit 5031 such that the position and the posture of the endoscope 5001 are controlled. Consequently, stable fixation in position of the endoscope 5001 can be implemented.
(Endoscope)

The endoscope 5001 includes the lens barrel 5003 which has a region of a predetermined length from a distal end thereof to be inserted into a body cavity of the patient 5071, and a camera head 5005 connected to a proximal end of the lens barrel 5003. In the example depicted, the endoscope 5001 is depicted as a rigid endoscope having the lens barrel 5003 of the hard type. However, the endoscope 5001 may otherwise be configured as a flexible endoscope having the lens barrel 5003 of the flexible type.

The lens barrel 5003 has, at a distal end thereof, an opening in which an objective lens is fitted. A light source apparatus 5043 is connected to the endoscope 5001 such that light generated by the light source apparatus 5043 is introduced to a distal end of the lens barrel by a light guide extending in the inside of the lens barrel 5003 and is irradiated toward an observation target in a body cavity of the patient 5071 through the objective lens. It is to be noted that the endoscope 5001 may be a forward-viewing endoscope or may be an oblique-viewing endoscope or a side-viewing endoscope.

An optical system and an image pickup element are provided in the inside of the camera head 5005 such that reflected light (observation light) from an observation target is condensed on the image pickup element by the optical system. The observation light is photo-electrically converted by the image pickup element to generate an electric signal corresponding to the observation light, namely, an image signal corresponding to an observation image. The image signal is transmitted as RAW data to a CCU 5039. It is to be noted that the camera head 5005 has a function incorporated therein for suitably driving the optical system of the camera head 5005 to adjust the magnification and the focal distance.

It is to be noted that, in order to establish compatibility with, for example, a stereoscopic vision (three dimensional (3D) display), a plurality of image pickup elements may be provided on the camera head 5005. In this case, a plurality of relay optical systems are provided in the inside of the lens barrel 5003 in order to guide observation light to each of the plurality of image pickup elements.
(Various Apparatus Incorporated in Cart)

The CCU 5039 includes a central processing unit (CPU), a graphics processing unit (GPU) or the like and integrally controls operation of the endoscope 5001 and the display apparatus 5041. In particular, the CCU 5039 performs, for an image signal received from the camera head 5005, various image processes for displaying an image based on the image signal such as, for example, a development process (demosaic process). The CCU 5039 provides the image signal for which the image processes have been performed to the display apparatus 5041. Further, the CCU 5039 transmits a control signal to the camera head 5005 to control driving of the camera head 5005. The control signal may include information relating to an image pickup condition such as a magnification or a focal distance.

The display apparatus 5041 displays an image based on an image signal for which the image processes have been performed by the CCU 5039 under the control of the CCU 5039. If the endoscope 5001 is ready for imaging of a high resolution such as 4K (horizontal pixel number 3840× vertical pixel number 2160), 8K (horizontal pixel number 7680×vertical pixel number 4320) or the like and/or ready for 3D display, then a display apparatus by which corresponding display of the high resolution and/or 3D display are possible may be used as the display apparatus 5041. Where the apparatus is ready for imaging of a high resolution such as 4K or 8K, if the display apparatus used as the display apparatus 5041 has a size of equal to or not less than 55 inches, then a more immersive experience can be obtained. Further, a plurality of display apparatus 5041 having different resolutions and/or different sizes may be provided in accordance with purposes.

The light source apparatus 5043 includes a light source such as, for example, a light emitting diode (LED) and supplies irradiation light for imaging of a surgical region to the endoscope 5001.

The arm controlling apparatus 5045 includes a processor such as, for example, a CPU and operates in accordance with a predetermined program to control driving of the arm unit 5031 of the supporting arm apparatus 5027 in accordance with a predetermined controlling method.

An inputting apparatus 5047 is an input interface for the endoscopic surgery system 5000. A user can perform inputting of various kinds of information or instruction inputting to the endoscopic surgery system 5000 through the inputting apparatus 5047. For example, the user would input various kinds of information relating to surgery such as physical information of a patient, information regarding a surgical procedure of the surgery and so forth through the inputting apparatus 5047. Further, the user would input, for example, an instruction to drive the arm unit 5031, an instruction to change an image pickup condition (type of irradiation light, magnification, focal distance or the like) by the endoscope 5001, an instruction to drive the energy device 5021 or the like through the inputting apparatus 5047.

The type of the inputting apparatus 5047 is not limited and may be that of any one of various known inputting apparatus. As the inputting apparatus 5047, for example, a mouse, a keyboard, a touch panel, a switch, a foot switch 5057 and/or a lever or the like may be applied. Where a touch panel is used as the inputting apparatus 5047, it may be provided on the display face of the display apparatus 5041.

Otherwise, the inputting apparatus 5047 is a device to be mounted on a user such as, for example, a glasses type wearable device or a head mounted display (HMD), and various kinds of inputting are performed in response to a gesture or a line of sight of the user detected by any of the devices mentioned. Further, the inputting apparatus 5047 includes a camera which can detect a motion of a user, and various kinds of inputting are performed in response to a gesture or a line of sight of a user detected from a video imaged by the camera. Further, the inputting apparatus 5047 includes a microphone which can collect the voice of a user, and various kinds of inputting are performed by voice collected by the microphone. By configuring the inputting apparatus 5047 such that various kinds of information can be inputted in a contactless fashion in this manner, especially a user who belongs to a clean area (for example, the surgeon 5067) can operate an apparatus belonging to an unclean area in a contactless fashion. Further, since the user can operate an apparatus without releasing a possessed surgical tool from its hand, the convenience to the user is improved.

A treatment tool controlling apparatus 5049 controls driving of the energy device 5021 for cautery or incision of a tissue, sealing of a blood vessel or the like. A pneumoperitoneum apparatus 5051 feeds gas into a body cavity of the patient 5071 through the pneumoperitoneum tube 5019 to inflate the body cavity in order to secure the field of view of the endoscope 5001 and secure the working space for the surgeon. A recorder 5053 is an apparatus capable of recording various kinds of information relating to surgery. A printer 5055 is an apparatus capable of printing various kinds of information relating to surgery in various forms such as a text, an image or a graph.

In the following, especially a characteristic configuration of the endoscopic surgery system 5000 is described in more detail.

(Supporting Arm Apparatus)

The supporting arm apparatus 5027 includes the base unit 5029 serving as a base, and the arm unit 5031 extending from the base unit 5029. In the example depicted, the arm unit 5031 includes the plurality of joint portions 5033a, 5033b and 5033c and the plurality of links 5035a and 5035b connected to each other by the joint portion 5033b. In FIG. 1, for simplified illustration, the configuration of the arm unit 5031 is depicted in a simplified form. Actually, the shape, number and arrangement of the joint portions 5033a to 5033c and the links 5035a and 5035b and the direction and so forth of axes of rotation of the joint portions 5033a to 5033c can be set suitably such that the arm unit 5031 has a desired degree of freedom. For example, the arm unit 5031 may preferably be configured such that it has a degree of freedom equal to or not less than 6 degrees of freedom. This makes it possible to move the endoscope 5001 freely within the movable range of the arm unit 5031. Consequently, it becomes possible to insert the lens barrel 5003 of the endoscope 5001 from a desired direction into a body cavity of the patient 5071.

An actuator is provided in each of the joint portions 5033a to 5033c, and the joint portions 5033a to 5033c are configured such that they are rotatable around predetermined axes of rotation thereof by driving of the respective actuators. The driving of the actuators is controlled by the arm controlling apparatus 5045 to control the rotational angle of each of the joint portions 5033a to 5033c thereby to control driving of the arm unit 5031. Consequently, control of the position and the posture of the endoscope 5001 can be implemented. Thereupon, the arm controlling apparatus 5045 can control driving of the arm unit 5031 by various known controlling methods such as force control or position control.

For example, if the surgeon 5067 suitably performs operation inputting through the inputting apparatus 5047 (including the foot switch 5057), then driving of the arm unit 5031 may be controlled suitably by the arm controlling apparatus 5045 in response to the operation input to control the position and the posture of the endoscope 5001. After the endoscope 5001 at the distal end of the arm unit 5031 is moved from an arbitrary position to a different arbitrary position by the control just described, the endoscope 5001 can be supported fixedly at the position after the movement. It is to be noted that the arm unit 5031 may be operated in a master-slave fashion. In this case, the arm unit 5031 may be remotely controlled by the user through the inputting apparatus 5047 which is placed at a place remote from the operating room.

Further, where force control is applied, the arm controlling apparatus 5045 may perform power-assisted control to drive the actuators of the joint portions 5033a to 5033c such that the arm unit 5031 may receive external force by the user and move smoothly following the external force. This makes it possible to move, when the user directly touches with and moves the arm unit 5031, the arm unit 5031 with comparatively weak force. Accordingly, it becomes possible for the user to move the endoscope 5001 more intuitively by a simpler and easier operation, and the convenience to the user can be improved.

Here, generally in endoscopic surgery, the endoscope 5001 is supported by a medical doctor called scopist. In contrast, where the supporting arm apparatus 5027 is used, the position of the endoscope 5001 can be fixed more certainly without hands, and therefore, an image of a surgical region can be obtained stably and surgery can be performed smoothly.

It is to be noted that the arm controlling apparatus 5045 may not necessarily be provided on the cart 5037. Further, the arm controlling apparatus 5045 may not necessarily be a single apparatus. For example, the arm controlling apparatus 5045 may be provided in each of the joint portions 5033a to 5033c of the arm unit 5031 of the supporting arm apparatus 5027 such that the plurality of arm controlling apparatus 5045 cooperate with each other to implement driving control of the arm unit 5031.

(Light Source Apparatus)

The light source apparatus 5043 supplies irradiation light upon imaging of a surgical region to the endoscope 5001. The light source apparatus 5043 includes a white light source which includes, for example, an LED, a laser light source or a combination of them. In this case, where a white light source includes a combination of red, green, and blue (RGB) laser light sources, since the output intensity and the output timing can be controlled with a high degree of accuracy for each color (each wavelength), adjustment of the white balance of a picked up image can be performed by the light source apparatus 5043. Further, in this case, if laser beams from the respective RGB laser light sources are irradiated time-divisionally on an observation target and driving of the image pickup elements of the camera head 5005 is controlled in synchronism with the irradiation timings, then images individually corresponding to the R, G and B colors can be picked up time-divisionally. According to the method just described, a color image can be obtained even if a color filter is not provided for the image pickup element.

Further, driving of the light source apparatus 5043 may be controlled such that the intensity of light to be outputted is changed for each predetermined time. By controlling driving of the image pickup element of the camera head 5005 in synchronism with the timing of the change of the intensity of light to acquire images time-divisionally and synthesizing the images, an image of a high dynamic range free from underexposed blocked up shadows and overexposed highlights can be created.

Further, the light source apparatus 5043 may be configured to supply light of a predetermined wavelength band ready for special light observation. In special light observation, for example, by utilizing the wavelength dependency of absorption of light in a body tissue to irradiate light of a narrower wavelength band in comparison with irradiation light upon ordinary observation (namely, white light), narrow band light observation (narrow band imaging) of imaging a predetermined tissue such as a blood vessel of a superficial portion of the mucous membrane or the like in a high contrast is performed. Alternatively, in special light observation, fluorescent observation for obtaining an image from fluorescent light generated by irradiation of excitation light may be performed. In fluorescent observation, it is possible to perform observation of fluorescent light from a body tissue by irradiating excitation light on the body tissue (autofluorescence observation) or to obtain a fluorescent light image by locally injecting a reagent such as indocyanine green (ICG) into a body tissue and irradiating excitation light corresponding to a fluorescent light wavelength of the reagent upon the body tissue. The light source apparatus 5043 can be configured to supply such narrow-band light and/or excitation light suitable for special light observation as described above.

(Camera Head and CCU)

Figure 2:
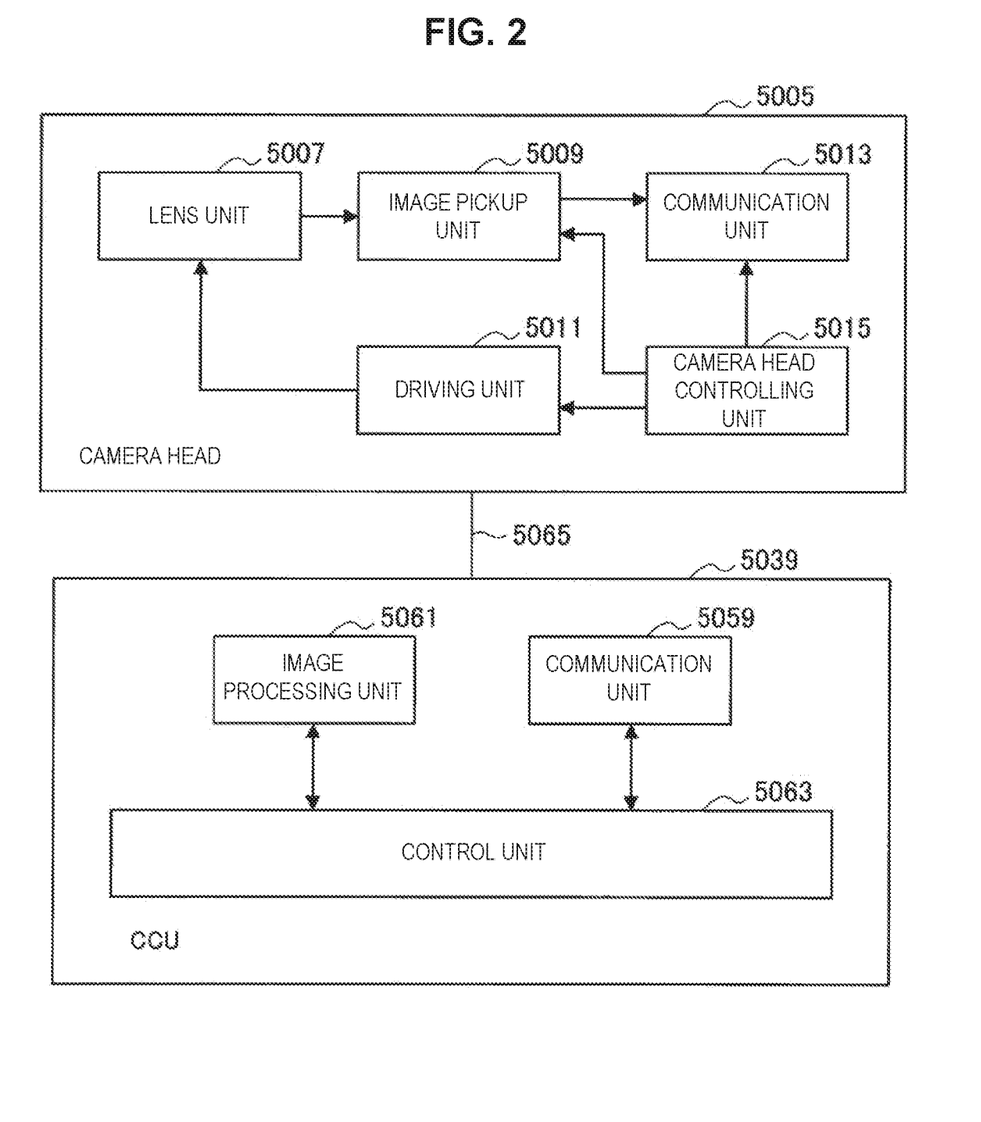
FIG. 2 is a block diagram depicting an example of a functional configuration of a camera head and a camera control unit (CCU) depicted in FIG. 1.

Functions of the camera head 5005 of the endoscope 5001 and the CCU 5039 are described in more detail with reference to FIG. 2. FIG. 2 is a block diagram depicting an example of a functional configuration of the camera head 5005 and the CCU 5039 depicted in FIG. 1.

Referring to FIG. 2, the camera head 5005 has, as functions thereof, a lens unit 5007, an image pickup unit 5009, a driving unit 5011, a communication unit 5013 and a camera head controlling unit 5015. Further, the CCU 5039 has, as functions thereof, a communication unit 5059, an image processing unit 5061 and a control unit 5063. The camera head 5005 and the CCU 5039 are connected to be bidirectionally communicable to each other by a transmission cable 5065.

First, a functional configuration of the camera head 5005 is described. The lens unit 5007 is an optical system provided at a connecting location of the camera head 5005 to the lens barrel 5003. Observation light taken in from a distal end of the lens barrel 5003 is introduced into the camera head 5005 and enters the lens unit 5007. The lens unit 5007 includes a combination of a plurality of lenses including a zoom lens and a focusing lens. The lens unit 5007 has optical properties adjusted such that the observation light is condensed on a light receiving face of the image pickup element of the image pickup unit 5009. Further, the zoom lens and the focusing lens are configured such that the positions thereof on their optical axis are movable for adjustment of the magnification and the focal point of a picked up image.

The image pickup unit 5009 includes an image pickup element and disposed at a succeeding stage to the lens unit 5007. Observation light having passed through the lens unit 5007 is condensed on the light receiving face of the image pickup element, and an image signal corresponding to the observation image is generated by photoelectric conversion of the image pickup element. The image signal generated by the image pickup unit 5009 is provided to the communication unit 5013.

As the image pickup element which is included by the image pickup unit 5009, an image sensor, for example, of the complementary metal oxide semiconductor (CMOS) type is used which has a Bayer array and is capable of picking up an image in color. It is to be noted that, as the image pickup element, an image pickup element may be used which is ready, for example, for imaging of an image of a high resolution equal to or not less than 4K. If an image of a surgical region is obtained in a high resolution, then the surgeon 5067 can comprehend a state of the surgical region in enhanced details and can proceed with the surgery more smoothly.

Further, the image pickup element which is included by the image pickup unit 5009 includes such that it has a pair of image pickup elements for acquiring image signals for the right eye and the left eye compatible with 3D display. Where 3D display is applied, the surgeon 5067 can comprehend the depth of a living body tissue in the surgical region more accurately. It is to be noted that, if the image pickup unit 5009 is configured as that of the multi-plate type, then a plurality of systems of lens units 5007 are provided corresponding to the individual image pickup elements of the image pickup unit 5009.

The image pickup unit 5009 may not necessarily be provided on the camera head 5005. For example, the image pickup unit 5009 may be provided just behind the objective lens in the inside of the lens barrel 5003.

The driving unit 5011 includes an actuator and moves the zoom lens and the focusing lens of the lens unit 5007 by a predetermined distance along the optical axis under the control of the camera head controlling unit 5015. Consequently, the magnification and the focal point of a picked up image by the image pickup unit 5009 can be adjusted suitably.

The communication unit 5013 includes a communication apparatus for transmitting and receiving various kinds of information to and from the CCU 5039. The communication unit 5013 transmits an image signal acquired from the image pickup unit 5009 as RAW data to the CCU 5039 through the transmission cable 5065. Thereupon, in order to display a picked up image of a surgical region in low latency, preferably the image signal is transmitted by optical communication. This is because, upon surgery, the surgeon 5067 performs surgery while observing the state of an affected area through a picked up image, it is demanded for a moving image of the surgical region to be displayed on the real time basis as far as possible in order to achieve surgery with a higher degree of safety and certainty. Where optical communication is applied, a photoelectric conversion module for converting an electric signal into an optical signal is provided in the communication unit 5013. After the image signal is converted into an optical signal by the photoelectric conversion module, it is transmitted to the CCU 5039 through the transmission cable 5065.

Further, the communication unit 5013 receives a control signal for controlling driving of the camera head 5005 from the CCU 5039. The control signal includes information relating to image pickup conditions such as, for example, information that a frame rate of a picked up image is designated, information that an exposure value upon image picking up is designated and/or information that a magnification and a focal point of a picked up image are designated. The communication unit 5013 provides the received control signal to the camera head controlling unit 5015. It is to be noted that also the control signal from the CCU 5039 may be transmitted by optical communication. In this case, a photoelectric conversion module for converting an optical signal into an electric signal is provided in the communication unit 5013. After the control signal is converted into an electric signal by the photoelectric conversion module, it is provided to the camera head controlling unit 5015.

It is to be noted that the image pickup conditions such as the frame rate, exposure value, magnification or focal point are set automatically by the control unit 5063 of the CCU 5039 on the basis of an acquired image signal. In other words, an auto exposure (AE) function, an auto focus (AF) function and an auto white balance (AWB) function are incorporated in the endoscope 5001.

The camera head controlling unit 5015 controls driving of the camera head 5005 on the basis of a control signal from the CCU 5039 received through the communication unit 5013. For example, the camera head controlling unit 5015 controls driving of the image pickup element of the image pickup unit 5009 on the basis of information that a frame rate of a picked up image is designated and/or information that an exposure value upon image picking up is designated. Further, for example, the camera head controlling unit 5015 controls the driving unit 5011 to suitably move the zoom lens and the focus lens of the lens unit 5007 on the basis of information that a magnification and a focal point of a picked up image are designated. The camera head controlling unit 5015 may further include a function for storing information for identifying the lens barrel 5003 and/or the camera head 5005.

It is to be noted that, by disposing the components such as the lens unit 5007 and the image pickup unit 5009 in a sealed structure having high airtightness and waterproof, the camera head 5005 can be provided with resistance to an autoclave sterilization process.

Now, a functional configuration of the CCU 5039 is described. The communication unit 5059 includes a communication apparatus for transmitting and receiving various kinds of information to and from the camera head 5005. The communication unit 5059 receives an image signal transmitted thereto from the camera head 5005 through the transmission cable 5065. Thereupon, the image signal may be transmitted preferably by optical communication as described above. In this case, for the compatibility with optical communication, the communication unit 5059 includes a photoelectric conversion module for converting an optical signal into an electric signal. The communication unit 5059 provides the image signal after conversion into an electric signal to the image processing unit 5061.

Further, the communication unit 5059 transmits, to the camera head 5005, a control signal for controlling driving of the camera head 5005. The control signal may also be transmitted by optical communication.

The image processing unit 5061 performs various image processes for an image signal in the form of RAW data transmitted thereto from the camera head 5005. The image processes include various known signal processes such as, for example, a development process, an image quality improving process (a bandwidth enhancement process, a super-resolution process, a noise reduction (NR) process and/or an image stabilization process) and/or an enlargement process (electronic zooming process). Further, the image processing unit 5061 performs a detection process for an image signal in order to perform AE, AF and AWB.

The image processing unit 5061 includes a processor such as a CPU or a GPU, and when the processor operates in accordance with a predetermined program, the image processes and the detection process described above can be performed. It is to be noted that, where the image processing unit 5061 includes a plurality of GPUs, the image processing unit 5061 suitably divides information relating to an image signal such that image processes are performed in parallel by the plurality of GPUs.

The control unit 5063 performs various kinds of control relating to image picking up of a surgical region by the endoscope 5001 and display of the picked up image. For example, the control unit 5063 generates a control signal for controlling driving of the camera head 5005. Thereupon, if image pickup conditions are inputted by the user, then the control unit 5063 generates a control signal on the basis of the input by the user. Alternatively, where the endoscope 5001 has an AE function, an AF function and an AWB function incorporated therein, the control unit 5063 suitably calculates an optimum exposure value, focal distance and white balance in response to a result of a detection process by the image processing unit 5061 and generates a control signal.

Further, the control unit 5063 controls the display apparatus 5041 to display an image of a surgical region on the basis of an image signal for which image processes have been performed by the image processing unit 5061. Thereupon, the control unit 5063 recognizes various objects in the surgical region image using various image recognition technologies. For example, the control unit 5063 can recognize a surgical tool such as forceps, a particular living body region, bleeding, mist when the energy device 5021 is used and so forth by detecting the shape, color and so forth of edges of the objects included in the surgical region image. The control unit 5063 causes, when it controls the display unit 5041 to display a surgical region image, various kinds of surgery supporting information to be displayed in an overlapping manner with an image of the surgical region using a result of the recognition. Where surgery supporting information is displayed in an overlapping manner and presented to the surgeon 5067, the surgeon 5067 can proceed with the surgery more safety and certainty.

The transmission cable 5065 which connects the camera head 5005 and the CCU 5039 to each other is an electric signal cable ready for communication of an electric signal, an optical fiber ready for optical communication or a composite cable ready for both of electrical and optical communication.

Here, while, in the example depicted, communication is performed by wired communication using the transmission cable 5065, the communication between the camera head 5005 and the CCU 5039 may be performed otherwise by wireless communication. Where the communication between the camera head 5005 and the CCU 5039 is performed by wireless communication, there is no necessity to lay the transmission cable 5065 in the operating room. Therefore, such a situation that movement of medical staff in the operating room is disturbed by the transmission cable 5065 can be eliminated.

An example of the endoscopic surgery system 5000 to which the technology according to an embodiment of the present disclosure can be applied has been described above. It is to be noted here that, although the endoscopic surgery system 5000 has been described as an example, the system to which the technology according to an embodiment of the present disclosure can be applied is not limited to the example. For example, the technology according to an embodiment of the present disclosure may be applied to a flexible endoscopic system for inspection or a microscopic surgery system.

2. Basic Configuration of Oblique-Viewing Endoscope

Figure 3:
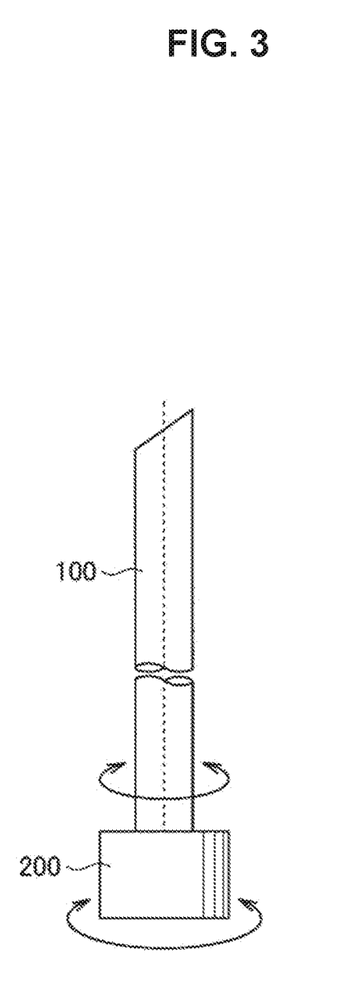
FIG. 3 is a schematic diagram depicting a configuration of an oblique-viewing endoscope according to an embodiment of the present disclosure.

FIG. 3 is a schematic diagram depicting the configuration of the oblique-viewing endoscope 100 according to an embodiment of the present disclosure. As depicted in FIG. 3, the oblique-viewing endoscope 100 is mounted on the distal end of a camera head 200. The oblique-viewing endoscope 100 corresponds to the lens barrel 5003 described with reference to FIGS. 1 and 2, and the camera head 200 corresponds to the camera head 5005 described with reference to FIG. 1 and FIG. 2. The oblique-viewing endoscope 100 and the camera head 200 are each capable of independently pivoting. Actuators are provided between the oblique-viewing endoscope 100 and the camera head 200, similarly to the respective joint portions 5033*a*, 5033*b* and 5033*c*. The oblique-viewing endoscope 100 is rotated with respect to the camera head 200 by the driven actuator. This causes a rotation angle $\theta_Z$ described below to be controlled.

The oblique-viewing endoscope 100 is supported by the supporting arm apparatus 5027. The supporting arm apparatus 5027 has functions for holding the oblique-viewing endoscope 100 in place of a scopist, and moving the oblique-viewing endoscope 100 according to an operation of a surgeon or an assistant such that a desired part can be observed.

Figure 4:
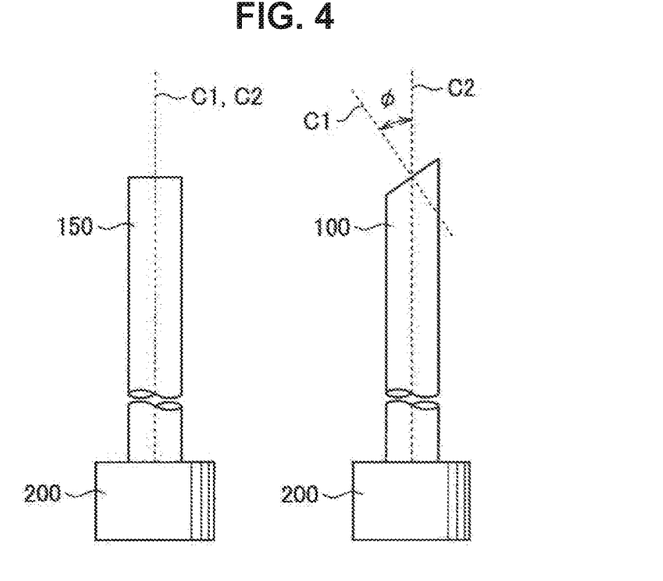
FIG. 4 is a schematic diagram depicting an oblique-viewing endoscope and a forward-viewing endoscope for comparison.

FIG. 4 is a schematic diagram depicting the oblique-viewing endoscope 100 and a forward-viewing endoscope 150 for comparison. An orientation (C1) of the objective lens of the forward-viewing endoscope 150 to a subject agrees with a longitudinal direction (C2) of the forward-viewing endoscope 150. In contrast, the orientation (C1) of the objective lens of the oblique-viewing endoscope 100 to a subject has a predetermined angle $\varphi$ to the longitudinal direction (C2) of the oblique-viewing endoscope 100.

Figure 5:
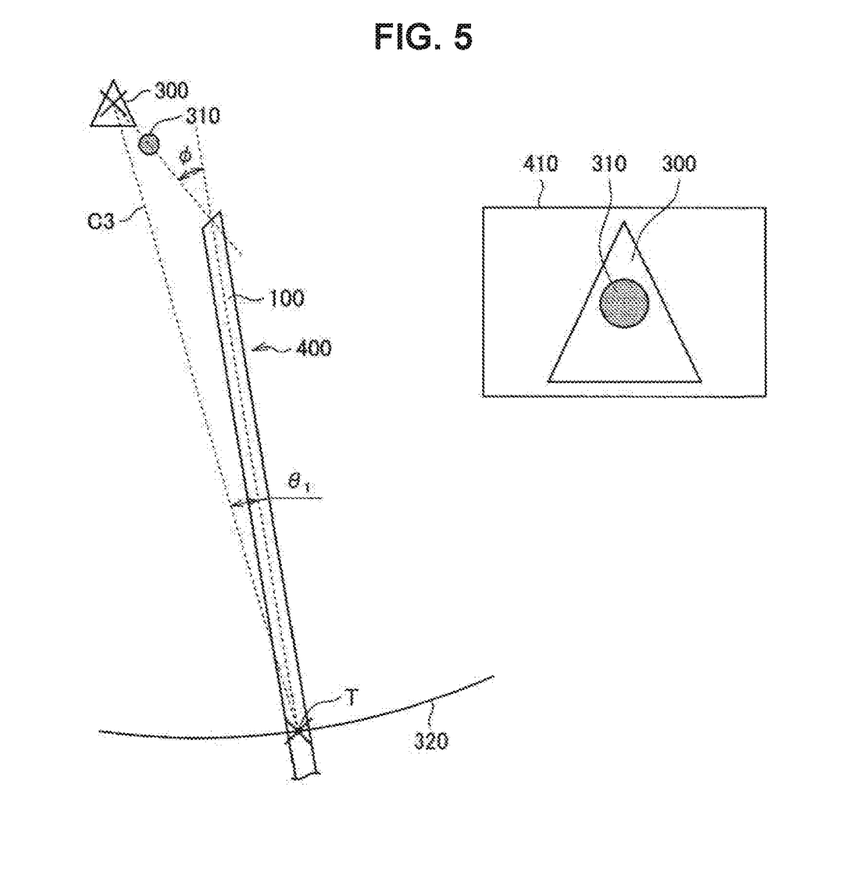
FIG. 5 is a schematic diagram depicting a situation in which an observation target object is observed with an oblique-viewing endoscope inserted into a human body from an abdominal wall.
Figure 6:
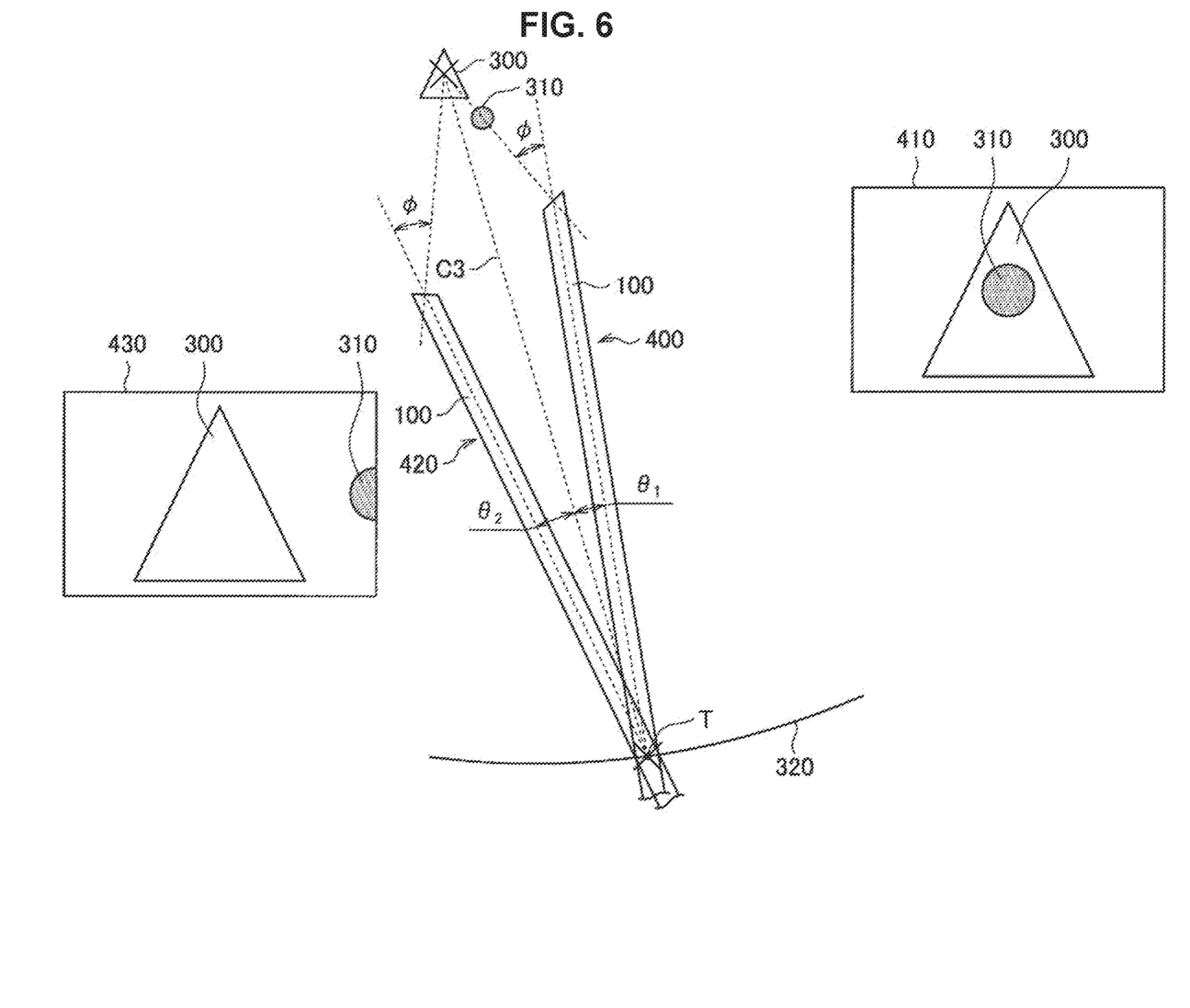
FIG. 6 is a schematic diagram depicting a situation in which an observation target object is observed with an oblique-viewing endoscope inserted into a human body from an abdominal wall.

FIGS. 5 and 6 are schematic diagrams each depicting the situation in which an observation target object 300 is observed with an oblique-viewing endoscope 100 inserted into the human body from an abdominal wall 320. In FIGS. 5 and 6, a trocar point T is a position at which a trocar 5025*a* is disposed, and represents a position at which the oblique-viewing endoscope 100 is inserted into the human body. A C3 direction depicted in FIGS. 5 and 6 is a direction that connects the trocar point T to the observation target object 300. In the case where an obstacle 310 such as an organ is present in front of the observation target object 300, the observation of the observation target object 300 with the forward-viewing endoscope 150 from the C3 direction depicted in FIGS. 5 and 6 fails to show the entire observation target object 300 because of the shade of the obstacle 310. FIG. 5 depicts a state 400 in which the oblique-viewing endoscope 100 is used and the insertion direction of the oblique-viewing endoscope 100 is different from the C3 direction, and a picked up image 410 picked up by the oblique-viewing endoscope 100 in the case of the state 400. Even in the case where the oblique-viewing endoscope 100 is used, the observation target object 300 is in the shade of the obstacle 310 in the state 400 depicted in FIG. 5.

Meanwhile, in addition to the state of FIG. 5, FIG. 6 depicts a state 420 in which the insertion direction of the oblique-viewing endoscope 100 is changed from the state 400 of FIG. 5 and the orientation of the objective lens is also changed, and a picked up image 430 in the case of the state 420. Changing the insertion direction of the oblique-viewing endoscope 100 and also changing the orientation of the objective lens like the state 420 of FIG. 6 make it possible to change a viewpoint and observe the observation target object 300 without being hidden by the obstacle 310.

Meanwhile, in generally, it is difficult to perform, in the case where the oblique-viewing endoscope 100 is about to be manually moved as depicted in FIG. 6 from the state 400 in which the observation target object 300 is hidden by the obstacle 310 to the state 420 in which the observation target object 300 is not hidden by the obstacle 310, an intuitive operation from the state 400 to the state 420 to image the observation target object 300 while keeping the state in which the observation target object 300 is positioned at the center of a picked up image. In addition, the existing endoscope supporting arm targets only the operation of the forward-viewing endoscope 150, but does not conform with any operation using the oblique-viewing endoscope 100 in the first place.

3. Control Over Oblique-Viewing Endoscope According to the Present Embodiment

In the present embodiment, the orientation of the oblique-viewing endoscope 100 is automatically adjusted with the supporting arm apparatus 5027 such that the observation target object 300 is disposed at the center of a picked up image when the observation target object 300 is caused to transition from the state 400 to the state 420 depicted in FIG. 6 not to be hidden by the obstacle 310. The detailed description will be made below.

Figure 7:
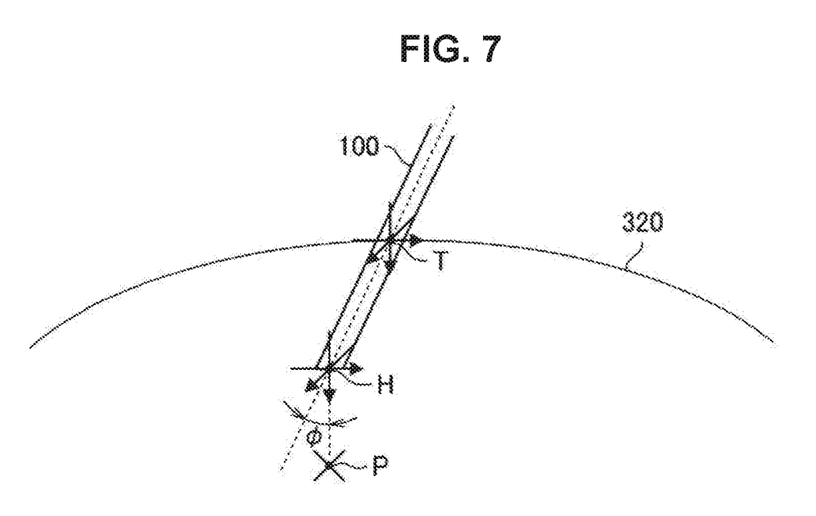
FIG. 7 is a schematic diagram depicting a state in which an oblique-viewing endoscope is inserted into a human body through an abdominal wall.

FIG. 7 is a schematic diagram depicting the state in which the oblique-viewing endoscope 100 is inserted into the human body through the abdominal wall 320. The trocar 5025*a* (not depicted) is disposed at the perforation position (trocar point T) of the oblique-viewing endoscope 100 on the abdominal wall 320, and the oblique-viewing endoscope 100 is inserted into the human body through the trocar 5025*a*.

FIG. 7 depicts the setting of a coordinate system in the body. As the coordinate system in the body, a coordinate system T in which the trocar point T serves as an origin is set. In addition, the distal end of the oblique-viewing endoscope 100 is set as an origin H, and a coordinate system H along the optical axis direction (imaging direction) in which the objective lens faces is set. At this time, when the coordinates of a central point (subject's central point) P of a picked up image as viewed from the trocar point T are set as $P_T$, the coordinates $P_T$ can be expressed as a homogeneous transformation matrix as shown in the following (1) expression.

[Math. 1]

$$P_T = \text{Yaw}(\theta_z)\text{Roll}(\theta_x)\text{Pitch}(\theta_y)\text{Transfer}(0, 0, L)\text{Pitch}(\varphi)\begin{pmatrix}0\\0\\l\\1\end{pmatrix} = \begin{pmatrix}x_T\\y_T\\z_T\\1\end{pmatrix} \quad (1)$$

However, as the (1) expression, a homogeneous coordinate expression is shown in which $P_T$ is an element of $R^4$. $\theta x$, $\theta y$ and $\theta z$ are angles representing the insertion posture of the oblique-viewing endoscope at the trocar point T, and angles obtained by rotating around the axes of respective subscripts x, y and z. It is to be noted that it is possible in the coordinate system T to define for the x axis, the y axis, and the z axis, as an example, the z axis as a perpendicular direction, and an xy plane as a plane orthogonal to the z axis. Alternatively, it is also possible to define the z axis as the initial insertion direction of the oblique-viewing endoscope 100, and the xy plane as a plane orthogonal to the z axis. In addition, L represents the length of the oblique-viewing endoscope 100 inserted into the human body from the trocar point T. $\varphi$ represents the angle of the obliqueness of the objective lens, and l represents the distance from the objective lens to the imaging point. $\theta x$, $\theta y$, $\theta z$, L, and l at the time of beginning the present control calculation can be decided on the basis of the configuration of the supporting arm apparatus, so that the coordinates $P_T$ of an observation target can be specifically obtained by applying them to the expression (1).

In addition, Yaw, Roll, Pitch, and Transfer in the (1) expression each represent a homogeneous transformation matrix as follows. Yaw($\theta z$), Roll($\theta x$), and Pitch($\theta y$) in the (1) expression show how much oblique-viewing endoscope 100 is inclined against the x axis, the y axis, and the z axis. In addition, Transfer shows how much the oblique-viewing endoscope 100 is inserted into the human body.

[Math. 2]

$$\text{Roll}(\theta) := \begin{pmatrix}1 & 0 & 0 & 0\\0 & \cos\theta & -\sin\theta & 0\\0 & \sin\theta & \cos\theta & 0\\0 & 0 & 0 & 1\end{pmatrix}$$

$$\text{Pitch}(\theta) := \begin{pmatrix}\cos\theta & 0 & \sin\theta & 0\\0 & 1 & 0 & 0\\-\sin\theta & 0 & \cos\theta & 0\\0 & 0 & 0 & 1\end{pmatrix}$$

$$\text{Yaw}(\theta) := \begin{pmatrix}\cos\theta & -\sin\theta & 0 & 0\\\sin\theta & \cos\theta & 0 & 0\\0 & 0 & 1 & 0\\0 & 0 & 0 & 1\end{pmatrix}$$

$$\text{Transfer}(x, y, z) := \begin{pmatrix}1 & 0 & 0 & x\\0 & 1 & 0 & y\\0 & 0 & 1 & z\\0 & 0 & 0 & 1\end{pmatrix}$$

In the case where the observation target object 300 is observed with the posture changed from the state 400 to the state 420 depicted in FIG. 6, the movement of the oblique-viewing endoscope 100 in the direction along the abdominal wall 320 is restricted at the trocar point T. Therefore, a surgeon imparts a motion of rotating the oblique-viewing endoscope 100 around the trocar point T. That is, $\theta x$ and $\theta y$ among the parameters of the (1) expression are imparted as the parameter of new posture from the outside (surgeon). In the present embodiment, the remaining parameters are obtained with $\theta x$ and $\theta y$ used as known values such that a target subject (observation target object 300) remains at the center of a screen. Especially in the present embodiment, the insertion amount L of the oblique-viewing endoscope 100 into the human body from the trocar point T, and a rotational angle $\theta_Z$ of the oblique-viewing endoscope 100 around a Z axis at the coordinate system T are obtained. The supporting arm apparatus 5027 is operated on the basis of the insertion amount L and the rotational angle $\theta_Z$. This causes the observation target object 300 to be always positioned at the center of a screen when a surgeon imparts a motion of rotating the oblique-viewing endoscope 100 around the trocar point T.

A specific technique is shown as follows. Here, the coordinates $P_T$ of a central point P of a picked up image shown in the (1) expression are coordinates as viewed from the coordinate system T, but coordinates $P_H$ of the central point P of a picked up image as viewed from the coordinate system H can be expressed with $P_T$ in the (1) expression as the following (2) expression.

[Math. 3]

$$P_H = \text{Pitch}(-\varphi)\text{Transfer}(0, 0, -L) \quad (2)$$

$$\text{Pitch}(-\theta_y)\text{Roll}(-\theta_x)\text{Yaw}(-\theta_z)P_T = \begin{pmatrix}x_H\\y_H\\z_H\\1\end{pmatrix}$$

In the coordinate system H, the z axis direction serves as the optical axis direction of the objective lens of the oblique-viewing endoscope 100. Thus, a picked up image is an image corresponding to the xy plane. Therefore, in the (2) expression, the condition for positioning the observation target object 300 at the center of a screen corresponds to $(x_H, y_H)=(0, 0)$. In addition, in the present embodiment, as a constraint for two degrees of freedom that is missing because of four degrees of freedom in the body, the target value of $z_H$ is not set. With this arrangement, solving the two equations of $x_H=0$ and $y_H=0$ as equations to be solved offers the solutions of the insertion amount L and rotational angle $\theta_Z$ corresponding to the parameters $\theta x$ and $\theta y$ of new posture. As described above, L represents the insertion amount of the oblique-viewing endoscope 100 into the human body from the trocar point T, and $\theta_Z$ represents the rotational angle of the oblique-viewing endoscope 100 around the Z axis (longitudinal direction axis of the oblique-viewing endoscope 100) in the coordinate system T. The other parameters are known, so that obtaining L and $\theta_Z$ makes it possible to uniquely decide the position and posture of the oblique-viewing endoscope 100.

It is to be noted that the present embodiment uses a homogeneous transformation matrix to express an expression, but it is mathematically obvious that the similar calculation can also be expressed by using a rotation matrix with three rows and three columns and a three-dimensional vector. Further, as the order of rotation of coordinates, the above multiplies Yaw, Roll, and Pitch in this order from the left, but it is also possible to solve $(x_H, y_H)=(0, 0)$ even if any order is set as that order. In addition, the angle in the longitudinal direction to the optical axis direction of the objective lens of the oblique-viewing endoscope 100 is set as rotation of Pitch for the sake of convenience, but Yaw or Roll can also be selected for solution.

Figure 8:
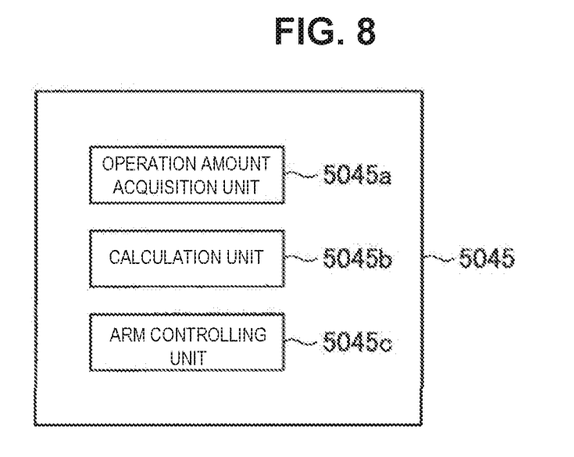
FIG. 8 is a schematic diagram depicting a configuration of an arm controlling apparatus 5045 that calculates an insertion amount L and a rotational angle $\theta_Z$ on the basis of a (1) expression and a (2) expression.

FIG. 8 is a schematic diagram depicting the configuration of the arm controlling apparatus 5045 that calculates the insertion amount L and the rotational angle $\theta_Z$ on the basis of the (1) expression and the (2) expression. As depicted in FIG. 8, the arm controlling apparatus 5045 includes an operation amount acquisition unit 5045a, a calculation unit 5045b, and an arm controlling unit 5045c. The configuration of the arm controlling apparatus 5045 depicted in FIG. 8 can include a circuit (hardware) or a central processing unit such as a CPU, and a program (software) for causing it to function. It is to be noted that the medical supporting arm according to the present embodiment includes the supporting arm apparatus 5027 that supports the oblique-viewing endoscope 100, and the arm controlling apparatus 5045. The supporting arm apparatus 5027 includes an active shaft (actuator) having seven or more degrees of freedom.

The operation amount acquisition unit 5045a acquires rotational angles $\theta x$ and $\theta y$. Actuators provided to the respective joint portions 5033a, 5033b and 5033c include encoders that detect the rotational angles of the respective joint portions 5033a, 5033b and 5033c. In addition, the rotational angle of the oblique-viewing endoscope 100 with respect to the camera head 200 is also detected by an encoder. This enables the arm controlling apparatus 5045 to sense the optical axis direction of the objective lens of the oblique-viewing endoscope 100. The operation amount acquisition unit 5045a can acquire the rotational angles $\theta x$ and $\theta y$ on the basis of the rotational angles detected by the encoders of the respective joint portions 5033a, 5033b and 5033c.

The calculation unit 5045b uses the (1) expression and (2) expression described above to calculate the insertion amount L and the rotational angle $\theta_Z$ on the basis of the rotational angles $\theta x$ and $\theta y$. At this time, the calculation unit 5045b sets the condition of $(x_H, y_H)=(0, 0)$ in the (2) expression, thereby calculating the insertion amount L and the rotational angle $\theta_Z$. It is to be noted that the observation target object 300 does not have to be disposed at the center of a picked up image, but may be disposed at a position off from the center. In this case, it is sufficient if any values are set as the values of $x_H$ and $y_H$.

The arm controlling unit 5045c controls the supporting arm apparatus 5027 on the basis of the insertion amount L and rotational angle $\theta_Z$ calculated by the calculation unit 5045b, and on the basis of the rotational angles $\theta x$ and $\theta y$ acquired by the operation amount acquisition unit 5045a. If the insertion amount L and the rotational angles $\theta x$, $\theta y$, and $\theta_Z$ are known, the driving control over the arm unit 5031 of the supporting arm apparatus 5027 can be performed by various known controlling methods such as force control or position control. It is to be noted that the driving of the supporting arm apparatus 5027 based on the insertion amount L and the rotational angles $\theta x$, $\theta y$, and $\theta_Z$ can also be performed manually by a surgeon using the insertion amount L and the rotational angles $\theta x$, $\theta y$, and $\theta_Z$ as operation amounts.

As described above, in the present embodiment, imaging can be possible from various directions while constructing the forward kinematic model of the oblique-viewing endoscope 100 in the body and keeping a desired place around a screen. At that time, with respect to the problem that the degree of freedom (DOF) in the body is 6 degrees of freedom, but actually four degrees of freedom to perform imaging from a completely arbitrary position and posture, setting a condition for putting a target point at the screen center and performing modeling make it possible to analytically solve an equation.

Figure 9:
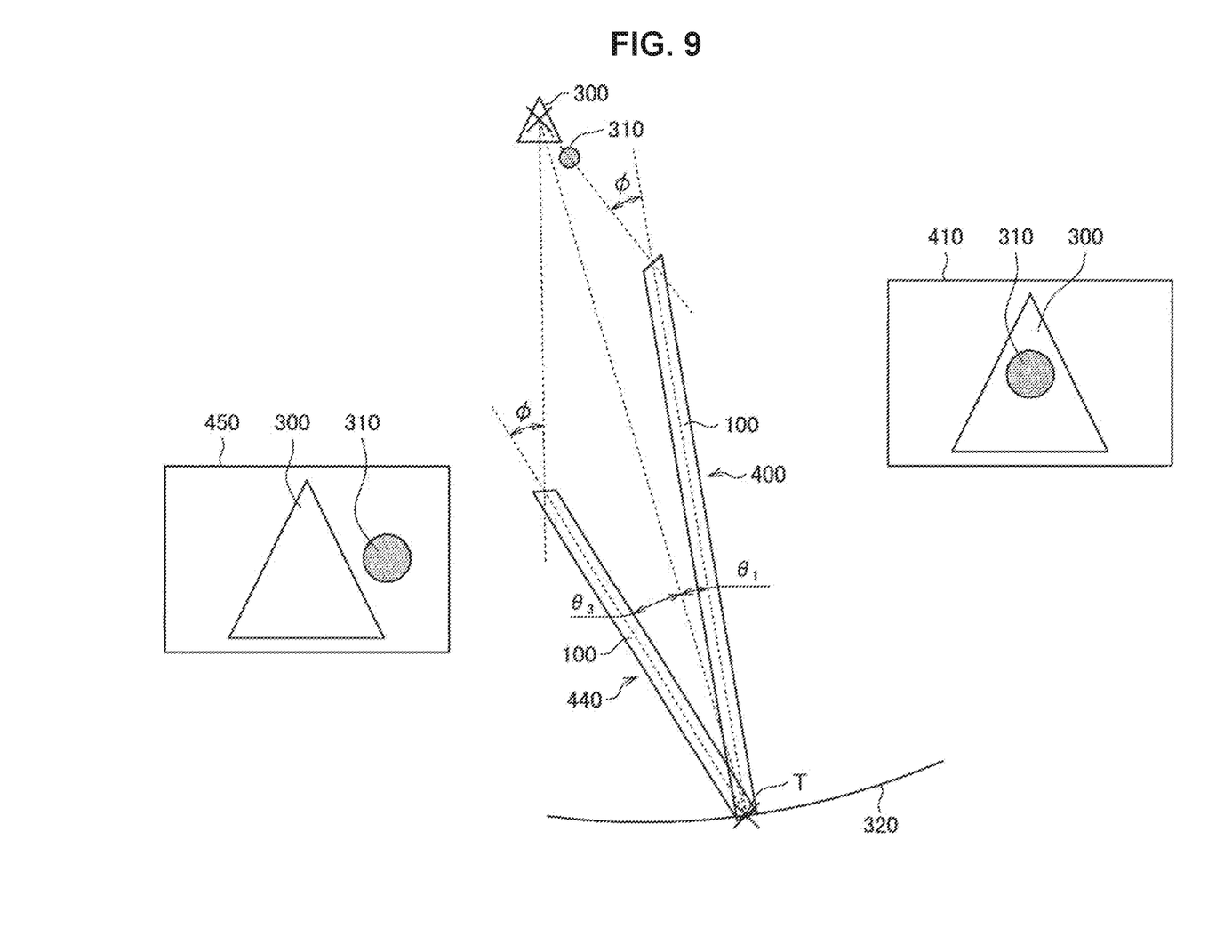
FIG. 9 is a schematic diagram depicting a state in which a surgeon moves the oblique-viewing endoscope from the state depicted in FIG. 6 in a direction for pulling out the oblique-viewing endoscope.

FIG. 9 depicts a state 440 in which a surgeon moves the oblique-viewing endoscope 100 from the state 420 depicted in FIG. 6 in a direction for pulling out the oblique-viewing endoscope 100, and a picked up image 450 in the case of the state 440. The calculation according to the (1) expression and the (2) expression enables the observation target object 300 to be positioned at the center of the picked up image 450 even in the case where the oblique-viewing endoscope 100 is moved as depicted in FIG. 9.

According to the present embodiment as described above, it is possible to always position, in the case where the oblique-viewing endoscope 100 is inserted into the human body, and the position and orientation of the oblique-viewing endoscope 100 are changed, a subject at the center of a picked up image. Thus, it is possible to significantly improve the operability of the oblique-viewing endoscope 100 by a surgeon.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)
A medical supporting arm including:
a supporting arm configured to support an oblique-viewing endoscope; and
a calculation unit configured to calculate a rotation angle of the oblique-viewing endoscope around an axis in a longitudinal direction, and an insertion amount of the oblique-viewing endoscope into a human body on the basis of a first expression that defines coordinates of a subject in a coordinate system in which an insertion opening allowing the oblique-viewing endoscope to be inserted into the human body serves as an origin, and a second expression that defines the coordinates of the subject positioned in an optical axis direction of an objective lens disposed at a distal end of the oblique-viewing endoscope in a coordinate system in which the distal end of the oblique-viewing endoscope serves as an origin.

(2)
The medical supporting arm according to (1), including:
an operation amount acquisition unit configured to acquire rotation of the oblique-viewing endoscope with the insertion opening serving as a supporting point as an operation amount of a surgeon, in which
the calculation unit calculates the rotation angle and the insertion amount on the basis of the operation amount.

(3)
The medical supporting arm according to (1) or (2), in which
the calculation unit calculates the rotation angle and the insertion amount on the basis of a condition for positioning the subject at a center of an optical axis of the objective lens in the second expression.

(4)
The medical supporting arm according to (1) or (2), in which
the calculation unit calculates the rotation angle and the insertion amount on the basis of a condition for positioning the subject within a predetermined distance from a center of an optical axis of the objective lens in the second expression.

(5)
The medical supporting arm according to any of (1) to (4), in which
the calculation unit calculates the rotation angle and the insertion amount on the basis of the first expression that defines first coordinates of the subject in a first coordinate system in which the insertion opening serves as an origin, and the second expression that defines the coordinates of the subject on the basis of the first coordinates in a second coordinate system in which the distal end of the oblique-viewing endoscope serves as an origin.

(6)
The medical supporting arm according to any of (1) to (5), further including:
an arm controlling unit configured to control the supporting arm on the basis of the rotation angle and the insertion amount.

(7)
A medical system including:
a camera head including an imaging unit that images a subject;
an oblique-viewing endoscope configured to be inserted into a human body, and be capable of rotating around an axis in an insertion direction with respect to the camera head;
a supporting arm configured to support the oblique-viewing endoscope; and
an arm controlling apparatus configured to control the supporting arm, in which
the arm controlling apparatus includes a calculation unit configured to calculate a rotation angle of the oblique-viewing endoscope around an axis in a longitudinal direction, and an insertion amount of the oblique-viewing endoscope into a human body on the basis of a first expression that defines coordinates of the subject in a coordinate system in which an insertion opening allowing the oblique-viewing endoscope to be inserted into the human body serves as an origin, and a second expression that defines the coordinates of the subject positioned in an optical axis direction of an objective lens disposed at a distal end of the oblique-viewing endoscope in a coordinate system in which the distal end of the oblique-viewing endoscope serves as an origin.

(8)
The medical system according to (7), in which
the arm controlling apparatus includes an operation amount acquisition unit configured to acquire rotation of the oblique-viewing endoscope with the insertion opening serving as a supporting point as an operation amount of a surgeon, and
the calculation unit calculates the rotation angle and the insertion amount on the basis of the operation amount.

(9)
The medical system according to (7) or (8), in which
the calculation unit calculates the rotation angle and the insertion amount on the basis of a condition for positioning the subject at a center of an optical axis of the objective lens in the second expression.

(10)
The medical system according to (7) or (8), in which
the calculation unit calculates the rotation angle and the insertion amount on the basis of a condition for positioning the subject within a predetermined distance from a center of an optical axis of the objective lens in the second expression.

(11)
The medical system according to any of (7) to (10), in which
the calculation unit calculates the rotation angle and the insertion amount on the basis of the first expression that defines first coordinates of the subject in a first coordinate system in which the insertion opening serves as an origin, and the second expression that defines the coordinates of the subject on the basis of the first coordinates in a second coordinate system in which the distal end of the oblique-viewing endoscope serves as an origin.

(12)
The medical system according to any of (7) to (11), in which
the arm controlling apparatus further includes an arm controlling unit configured to control the supporting arm on the basis of the rotation angle and the insertion amount.

REFERENCE SIGNS LIST

100 oblique-viewing endoscope
200 camera head
5027 supporting arm
5045 arm controlling apparatus
5045*a* operation amount acquisition unit
5045*b* calculation unit
5045*c* arm controlling unit

The invention claimed is:
1. A medical supporting arm apparatus, comprising: a supporting arm configured to support an oblique-viewing endoscope that is oriented towards a subject (i) in a human body and (ii) positioned in a direction of an optical axis of an objective lens disposed at a distal end of the oblique-viewing endoscope; and a processor configured to:
obtain first coordinates of the subject in the human body, in a first coordinate system, based on a posture of insertion of the oblique-viewing endoscope into the human body and an angle of obliqueness of the objective lens, and wherein, in the first coordinate system, an insertion opening that allows the oblique-viewing endoscope to be inserted into the human body serves as an origin;

obtain second coordinates of the subject in the human body, in a second coordinate system, based on the first coordinates, the posture of insertion of the oblique-viewing endoscope into the human body, and the angle of obliqueness of the objective lens, wherein, in the second coordinate system, the distal end of the oblique-viewing endoscope serves as an origin;

calculate, based on the first coordinates of the subject in the first coordinate system and the second coordinates of the subject in the second coordinate system, a rotation angle of the oblique-viewing endoscope around a first axis that is defined by a line from the insertion opening to the subject, and an insertion amount of the oblique-viewing endoscope into the human body; and control the supporting arm based on the rotation angle and the insertion amount to adjust an orientation of the oblique-viewing endoscope such that the subject is disposed at a center of a picked-up image of the subject.

2. The medical supporting arm apparatus according to claim 1, wherein the processor is further configured to:
acquire rotation of the oblique-viewing endoscope as an operation amount of a surgeon, wherein the acquired rotation is around a second axis that is different from the first axis and the insertion opening serves as a supporting point to the oblique-viewing endoscope; and
calculate the rotation angle of the oblique-viewing endoscope around the first axis and the insertion amount based on the operation amount.

3. The medical supporting arm apparatus according to claim 1, wherein the processor is further configured to:
calculate the rotation angle and the insertion amount based on a condition to position the subject at a center of the optical axis of the objective lens.

4. The medical supporting arm apparatus according to claim 1, wherein the processor is further configured to:
calculate the rotation angle and the insertion amount based on a condition to position the subject within a predetermined distance from a center of the optical axis of the objective lens.

5. The medical supporting arm apparatus according to claim 1, wherein the supporting arm comprises a plurality of joint portions, each rotatable around predetermined axes of rotations, and wherein the supporting arm is configured to move across a plurality of degrees of freedom at the plurality of joint portions.

6. The medical supporting arm apparatus according to claim 5, wherein the processor is further configured to control a movement of the supporting arm across the plurality of degrees of freedom based on the rotation angle and the insertion amount to adjust the orientation of the oblique-viewing endoscope.

7. The medical supporting arm apparatus according to claim 1, wherein the angle of obliqueness of the objective lens is an angle between the optical axis of the objective lens and the first axis that is in the longitudinal direction of the oblique-viewing endoscope.

8. A medical system comprising:
a camera head including an imaging unit that is configured to acquire an image of a subject in a human body;
an oblique-viewing endoscope configured to be inserted into the human body and oriented towards the subject positioned in a direction of an optical axis of an objective lens disposed at a distal end of the oblique-viewing endoscope;
a supporting arm configured to support the oblique-viewing endoscope; and an arm controlling apparatus configured to control the supporting arm,
wherein the arm controlling apparatus includes a processor configured to:
obtain first coordinates of the subject in the human body, in a first coordinate system, based on a posture of insertion of the oblique-viewing endoscope into the human body and an angle of obliqueness of the objective lens, and wherein, in the first coordinate system, an insertion opening that allows the oblique-viewing endoscope to be inserted into the human body serves as an origin;
obtain second coordinates of the subject in the human body, in a second coordinate system, based on the first coordinates, the posture of insertion of the oblique-viewing endoscope into the human body, and the angle of obliqueness of the objective lens, wherein, in the second coordinate system, the distal end of the oblique-viewing endoscope serves as an origin;
calculate, based on the first coordinates of the subject in the first coordinate system and the second coordinates of the subject in the second coordinate system, a rotation angle of the oblique-viewing endoscope around a first axis defined by a line from the insertion opening to the subject, and an insertion amount of the oblique-viewing endoscope into the human body; and,
control the supporting arm based on the rotation angle and the insertion amount to adjust an orientation of the oblique-viewing endoscope such that the subject is at a center of the acquired image of the subject.

9. The medical system according to claim 8, wherein the processor is further configured to:
acquire rotation of the oblique-viewing endoscope as an operation amount of a surgeon, wherein the acquired rotation is around a second axis that is different from the first axis and the insertion opening serves as a supporting point to the oblique-viewing endoscope; and
calculate the rotation angle of the oblique-viewing endoscope around the first axis and the insertion amount based on the operation amount.

10. The medical system according to claim 8, wherein the processor is further configured to:
calculate the rotation angle and the insertion amount based on a condition to position the subject at a center of the optical axis of the objective lens.

11. The medical system according to claim 8, wherein the processor is further configured to:
calculate the rotation angle and the insertion amount based on a condition to position the subject within a predetermined distance from a center of the optical axis of the objective lens.

* * * * *